US006666682B1

United States Patent
Meyerhof

(10) Patent No.: US 6,666,682 B1
(45) Date of Patent: Dec. 23, 2003

(54) INTRA-ORAL MIRROR

(76) Inventor: Peter G. Meyerhof, 684 W. Napa St., Sonoma, CA (US) 95476

( * ) Notice: Subject to any disclaimer, the term of this patent is extended or adjusted under 35 U.S.C. 154(b) by 15 days.

(21) Appl. No.: 09/989,501

(22) Filed: Nov. 20, 2001

(51) Int. Cl.[7] .............................................. A01G 1/00
(52) U.S. Cl. ....................................................... 433/31
(58) Field of Search ..................... 433/30, 31; 359/882; 600/246, 247

(56) References Cited

U.S. PATENT DOCUMENTS

| | | | | |
|---|---|---|---|---|
| 163,578 | A | * 5/1875 | Cogswell | .................... 433/30 |
| 1,345,718 | A | 7/1920 | Underwood | |
| 2,290,482 | A | 7/1942 | Neil | |
| 2,686,456 | A | * 8/1954 | Szuba et al. | .................. 433/30 |
| 3,162,191 | A | * 12/1964 | Canan | ........................ 600/246 |
| 3,539,247 | A | 11/1970 | Broussard | |
| 3,599,334 | A | 8/1971 | Warden | |
| 4,090,506 | A | * 5/1978 | Pilgrim | ...................... 600/246 |
| 4,252,522 | A | * 2/1981 | Petty et al. | ................... 433/30 |
| 4,294,356 | A | * 10/1981 | Abramowitz | ................ 433/30 |
| 4,500,169 | A | 2/1985 | Donnelly | |
| 4,512,635 | A | * 4/1985 | Melde | ......................... 433/30 |
| 4,610,629 | A | 9/1986 | Schrems et al. | |
| 4,900,253 | A | * 2/1990 | Landis | ......................... 433/30 |
| 5,052,690 | A | * 10/1991 | Sharp | ......................... 359/882 |
| 5,052,925 | A | 10/1991 | Stalcup | |
| 5,076,784 | A | 12/1991 | Jensen | |
| 5,926,328 | A | 7/1999 | Fabian | |
| 6,027,219 | A | 2/2000 | Arambulo | |
| 6,069,340 | A | 5/2000 | DeCanio | |

* cited by examiner

*Primary Examiner*—Tod E. Manahan
(74) *Attorney, Agent, or Firm*—Reed Smith Crosby Heafey LLP; John W. Carpenter

(57) ABSTRACT

An improved dental mirror for facilitating the accurate visualization and measurement of structures and distances and for facilitating the assessment of parallelism between non-adjacent teeth. The dental mirror includes an elongated handle having a longitudinal axis and affixed to one end thereof is a mirror frame. The mirror frame supports a planar mirror of rectangular geometry having a perimeter defined by a pair of major parallel edges and minor edges. A series of calibrations are provided along the perimeter of the mirror whereby at least one of the edges is calibrated by lines of demarcation. A plurality of angulations between handle axis and major parallel edge, in the plane of the mirror, is achievable by a rotation mechanism or on a series of fixed angle dental mirrors with different orientations.

21 Claims, 4 Drawing Sheets

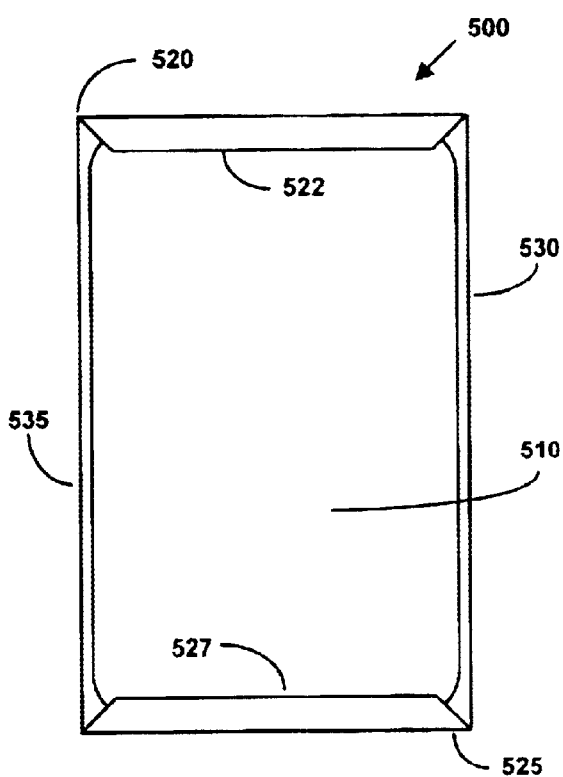
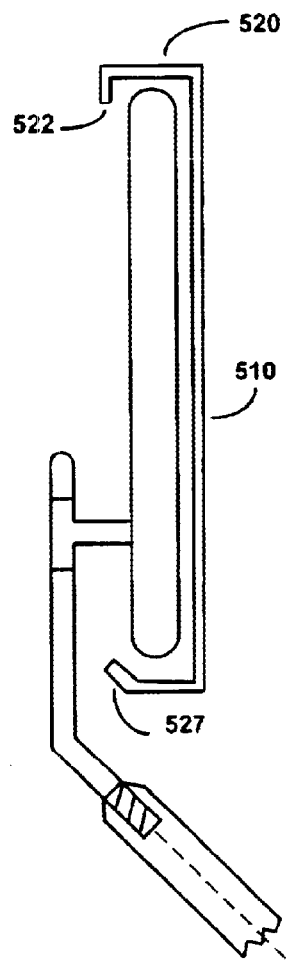
Fig. 5A
Fig. 5B

US 6,666,682 B1

INTRA-ORAL MIRROR

TECHNICAL FIELD OF INVENTION

The present invention is directed to an improved dental mirror that facilitates the accurate visualization and measurement of structures and distances and that facilitates the assessment of parallelism between non-adjacent teeth.

BACKGROUND OF THE INVENTION

Traditionally, mouth mirrors are provided with round geometries as such mirrors are able to access areas in the mouth without abrading or otherwise aggravating the tissue. Although round mirrors are inexpensive to produce and provide the ideal contact perimeter for a patient's mouth, such mirrors are not without their own set of limitations. Round mirrors provide a limited field of vision requiring the dentist to move the mirror axially with respect to its handle in order to view large or non-adjacent surfaces. Furthermore, round mirrors are far from ideal in the fabrication of fixed or removable bridgework or in the placement of multiple implants or orthodontic brackets, for the clinician cannot see at once all of the involved structures.

It is noted that in the preparation of most teeth for a fixed bridge or a removable partial denture, there is ideally about 10° to 15° of taper in precisely the same direction on each tooth or guide plane, allowing a rigid metal or ceramic structure to fit accurately. Less taper will interfere with insertion. More taper will cause unnecessary pulpal trauma, structural weakness of the abutment teeth, and a reduction in the retention of the final restoration. The degree of parallelism between non-adjacent teeth is commonly estimated by carefully moving a small round dental mirror, generally 20 to 24 millimeters in diameter, back and forth from one tooth to another during the teeth preparation process, while attempting to maintain the mirror in exactly the same plane relative to the eye of the clinician. This tedious process introduces inaccuracies.

Large intra-oral mirrors, in the order of 60×100 millimeters, are designed for the photography of the entire occlusal plane of all teeth on one jaw. By virtue of their size, these mirrors, which lack a handle and frame, are not maneuverable and are not designed to accommodate the simultaneous placement of a dental drill and suction apparatus, as needed for operative procedures.

Numerical measurement of intra-oral structures, distances, and parallelism is commonly determined by visual estimation, by the tedious and lengthy preparation of impressions from which plaster models are produced and measured, or by the intra-oral placement of small rulers or periodontal probes. These less maneuverable rulers and probes often cannot be held immediately adjacent to the structures or space being measured.

SUMMARY OF THE INVENTION

The present invention is an improved dental mirror uniquely capable of facilitating the accurate visualization and measurement of structures and distances and for facilitating the assessment of parallelism between non-adjacent teeth. The dental mirror comprises an elongated handle having a longitudinal axis and affixed to at least one end thereof is a mirror frame supporting a mirror. Preferably, the mirror is a planar mirror of rectangular geometry having a perimeter defined by a pair of major parallel edges and minor parallel edges and a series of calibrations along said perimeter whereby at least one of the edges is calibrated by lines of demarcation. The invention also includes a mirror frame having calibrations thereon. An attachment device for securing the frame to the handle is either to be fixed in one of several predetermined angles or adjustable to allow swiveling through these angles.

BRIEF DESCRIPTION OF THE DRAWINGS

FIG. 5A presents an embodiment of the present invention in which the mirror includes a cover; and FIG. 5B is an illustration of an example embodiment of a cover.

DETAILED DESCRIPTION OF THE INVENTION

Figure 1:
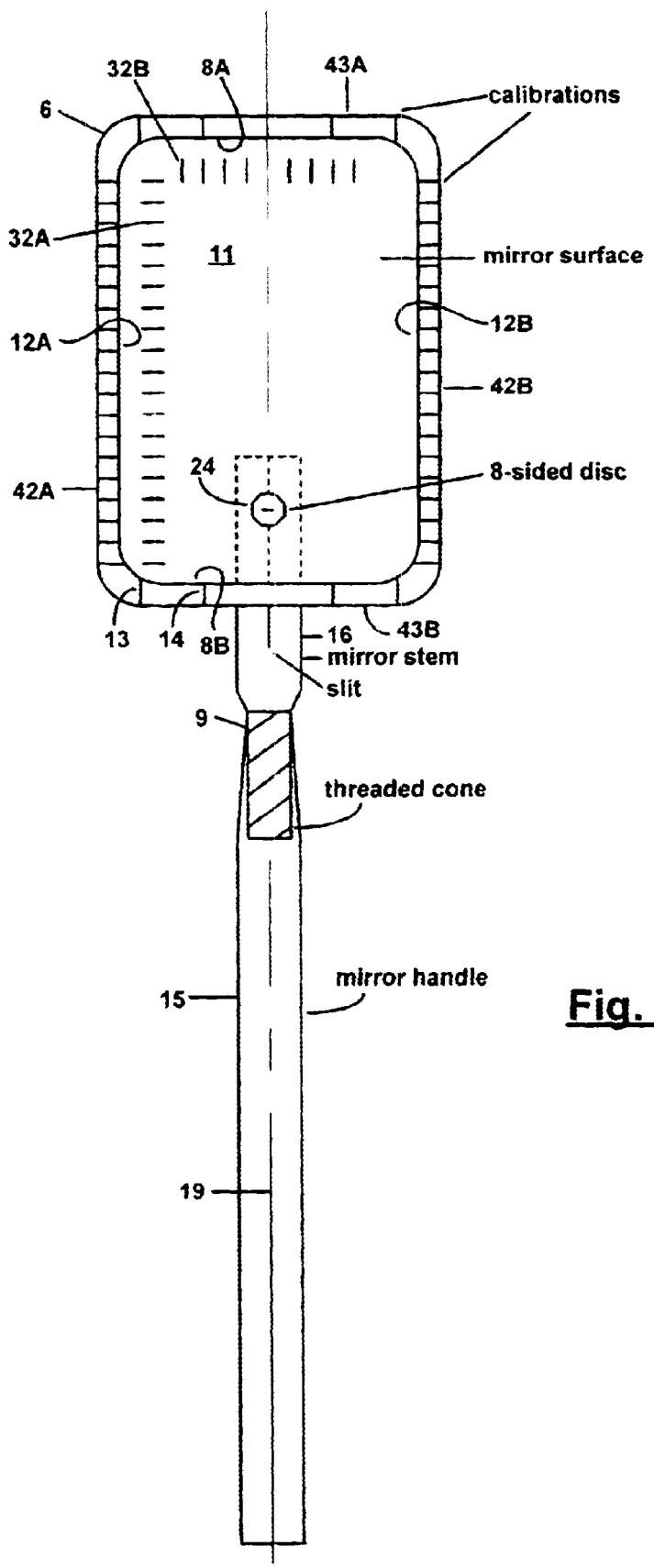
FIG. 1 is a plan view of the calibrated intra-oral mirror of the present invention.
Figure 2:
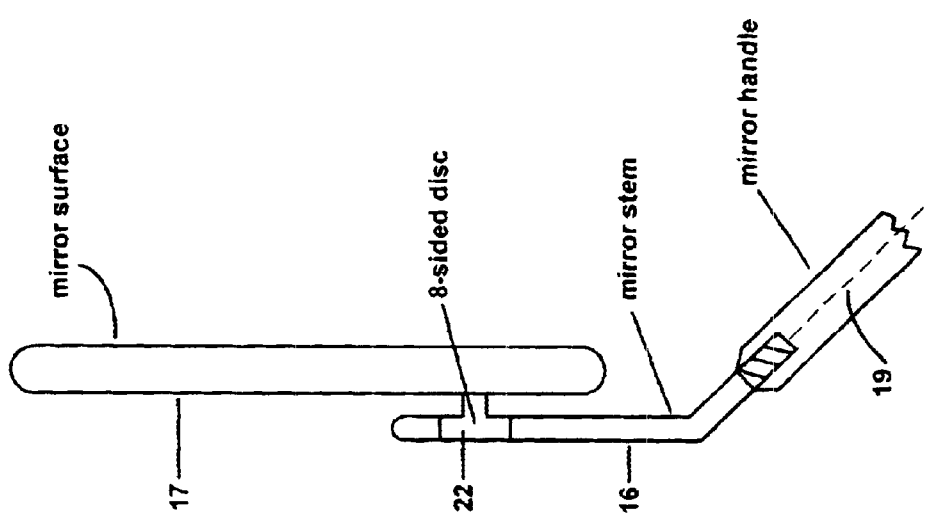
FIG. 2 is a partial side view of the calibrated intra-oral mirror of the present invention as depicted in FIG. 1.

In reference to FIG. 1, the present improved dental mirror for facilitating the accurate visualization and measurement of structures and distances and for hi facilitating the assessment of parallelism between non-adjacent teeth is depicted. Specifically, the present invention is provided with elongated handle 15 having longitudinal axis 19 and affixed to tapered end 9 is stem 16 which can be threadably engaged with handle 15 as shown. Mirror frame 17 (FIG. 2) can be attached directly to handle 15 via stem 16 to provide an angular relationship between frame 17 and longitudinal axis 19, as best depicted in FIG. 2.

Mirror frame 17 is employed to support planar mirror 11 of substantially rectangular geometry having a perimeter defined by a pair of major parallel edges 12A and 12B and minor parallel edges 8A and 8B. The preferred embodiment further includes a series of calibrations along the perimeter of mirror 11 whereby at least one major parallel edge and/or at least one minor parallel edge is calibrated by lines of demarcation 32A and 32B, respectively.

As a further preferred embodiment, mirror 11 can be completely captured by mirror frame 17, the latter being sized to be larger than the planar mirror thus creating a border composed of major edges 42A and 42B, minor edges 43A and 43B and rounded corners 6. When the preferred configuration such as that shown in FIG. 1 is employed, the said series of calibrations can be provided on the frame border as lines of demarcation 13, 14, etc., rather than on the mirror itself.

The invention as depicted in FIG. 1 shows mirror 11 and its major parallel edges 12A and 12B as being parallel to longitudinal axis 19. However, in practice, it is preferable for the visualization of most surfaces of the oral cavity to have major parallel edges 12A and 12B angled with respect to longitudinal axis 19 of handle 15. This makes for a more convenient tool for use by the clinician noting that the ideal angle between major parallel edges 12A and 12B and longitudinal axis 19 is approximately 45°. This angle can be rigidly established between mirror 11 and handle 15. Alternatively, mirror 11 can be made rotatably adjustable with regard to handle 15 in the plane of the mirror surface as best depicted in FIG. 3.

Figure 3:
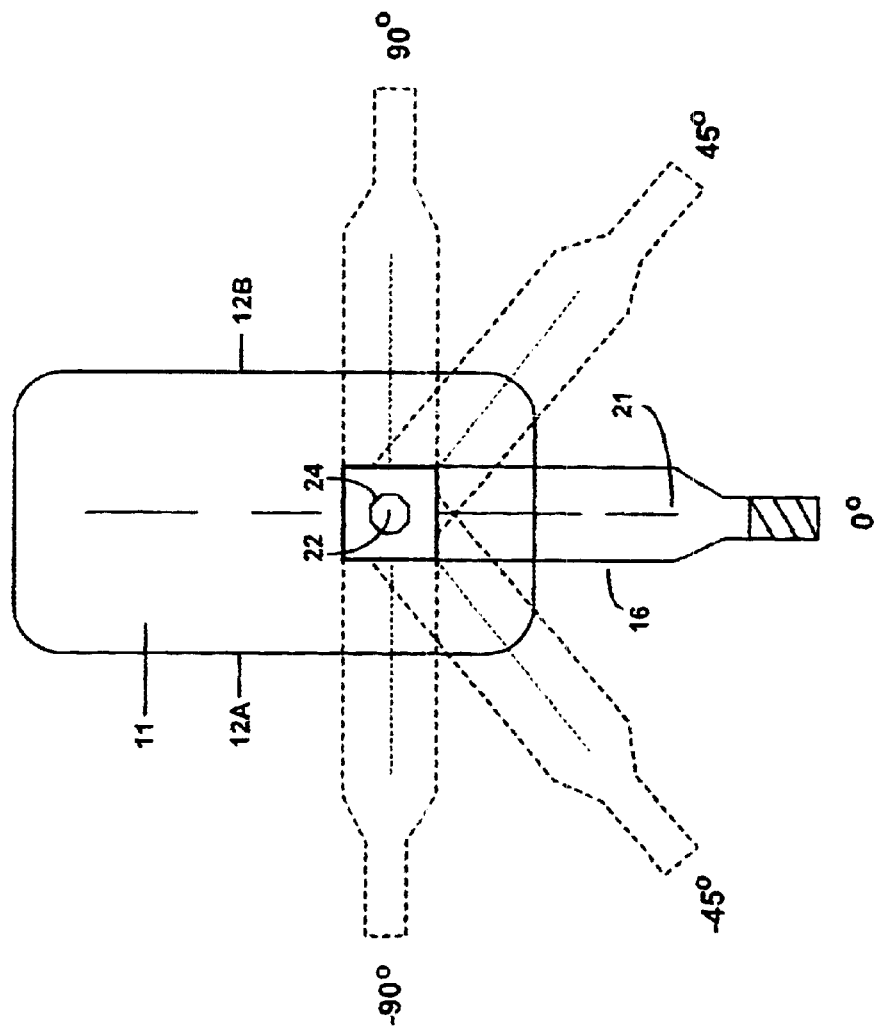
FIG. 3 is a partial plan view of the calibrated intra-oral mirror of the present invention depicting a preferred embodiment and without depicting the handle portion of the invention.

FIG. 3 shows a planar mirror 11 having major parallel edges 12A and 12B substantially parallel to longitudinal axis 19. However, this orientation can be varied by providing stub 22 emanating from mirror frame 17 which mates with opening 24 found within handle stem 16. In the embodiment depicted, stub 22 and mating opening 24 are each octagonal such that frame 11 as defined by parallel major edges 12A and 12B ratchet in 45° increments with respect to longitudinal axis 19. Obviously, this preferred embodiment employing an octagon to facilitate 45° increments can be altered to any other geometric orientation to provide relative movement between mirror 11 and mirror handle 15. In the embodiment as depicted, stem 16 is provided with slit 21 to enable stub 22 to ratchet within opening 24 whereby stub 22 spreads stem 16 between "click points" as slit 21 facilitates such movement. Preferably this adjustment mechanism, or another mounting mechanism that accomplishes the same result, has as few indentations, cavities, or protrusions as possible, making the instrument more easily cleaned and sterilized.

Although the dimensions of mirror 11 can vary to some extent, it has been determined that an ideal size would be a rectangle having major parallel edges of approximately 45 millimeters and minor parallel edges of approximately 25 millimeters. Mirror frame 17 should ideally be composed of a metal with rounded corners 6 provided to facilitate use in the oral cavity while minimizing damage to intra-oral tissues.

In addition to the above, and as an alternative to employing an embodiment whereby mirror 11 can be pivoted with regard to longitudinal axis 19 as depicted in FIG. 3, the clinician could be provided with a series of fixed, non-rotatable embodiments whereby a series of such mirrors would be characterized as having different orientations. The embodiment shown in FIG. 3 is an attempt to incorporate reasonably anticipated angular orientation possibilities in a single device. Further, it is contemplated that the present invention could include certain non-inventive expedients to assist its user without departing from the spirit and scope of the present invention.

Figure 4:
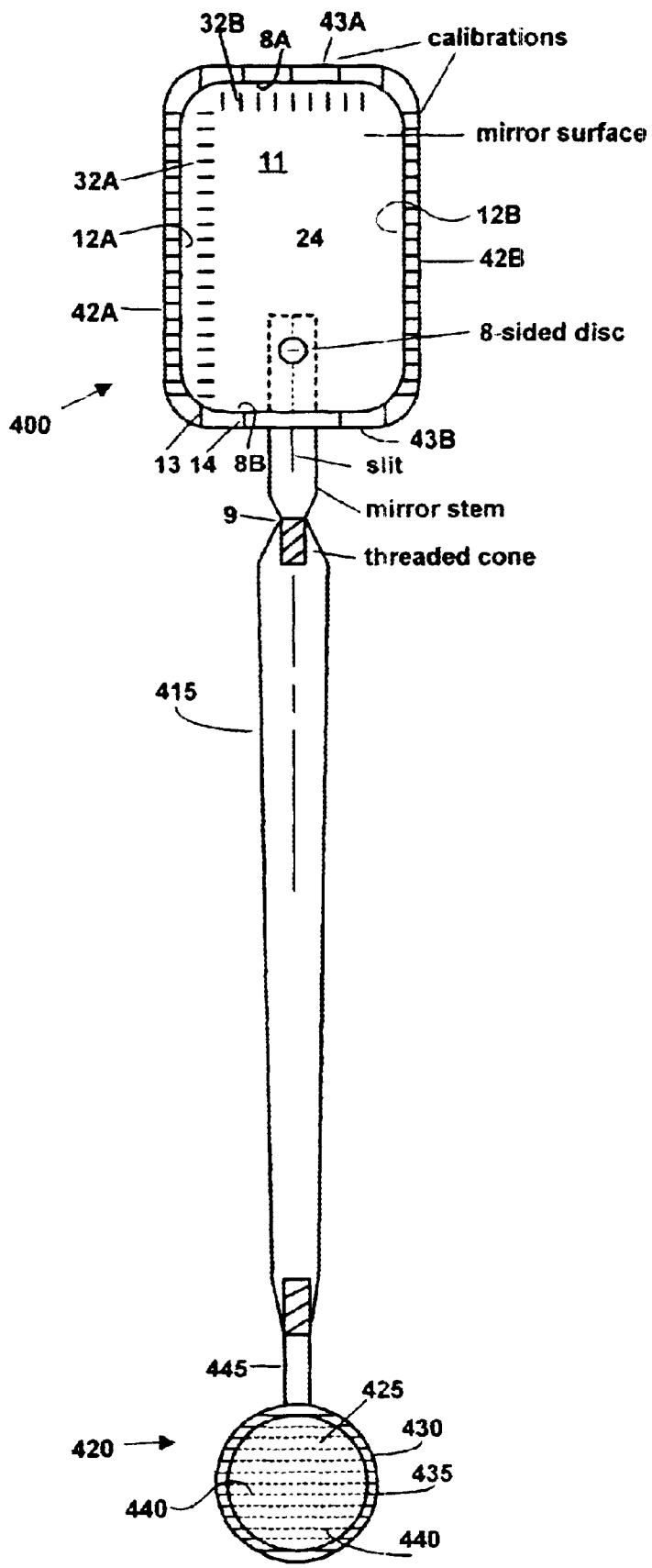
FIG. 4 is a drawing of an embodiment of the present invention attached to another dental instrument.

FIG. 4 is a drawing of an embodiment of the present invention, a dental mirror assembly 400 attached to a handle 415 which has a threaded cone socket at each end. One end of handle 415 mates with stem 445 emanating from another device which may be any dental instrument, including a periodontal probe, dental explorer, or another type of mirror. By attaching the present invention to an existing dental instrument, the dentist is provided with a convenient location for accessing an additional tool without need to interrupt work to retrieve the additional tool. In this example embodiment, the other device is a dental mirror 420 arranged according to another embodiment of the present invention.

Dental mirror assembly 420 is a mirror 425 set in a frame 430. In one embodiment, the frame 430 has calibrations 435 that are used for measurement as previously disclosed in the mirror of FIG. 1. The calibrations may be on one part of the frame surrounding mirror 425 or may be present on all parts of the frame. Alternatively, the calibrations are presented on the mirror 440. The calibrations may be one or more parallel lines etched (or painted) across the mirror, or the lines may be dashed. The dental mirror 420 may be attached via stem 445 set at a fixed angle, or the stem may incorporate an adjustment device that allows the angle between the mirror and handle to be changed in a plane perpendicular to the mirror surface. An angle of approximately 150° is generally satisfactory for this mirror except when observing the distal surfaces of the most posterior teeth in which case an angle close to 90° would be optimal.

In one embodiment, the frame of the mirror is colored, making the instrument more identifiable on an instrument tray particularly among a set of different fixed angle mirrors, and also more appealing to children, thereby relaxing them prior to use of an instrument that can result in anxiety. Any color may be used for the frame but preferably at least one shade of red, blue, yellow, or green (or any combination or mixture of colors).

FIG. 5A presents an embodiment of the present invention in which the mirror includes a cover 500. The cover 500 may be constructed from plastic or another material in order to protect the mirror from being scratched when not in use or during sterilization procedures. The cover is designed to easily snap on, or slide over, the mirror. Top snap 520 and bottom snap 525 snap over edges of the mirror (or frame) and secure the cover to the mirror. Top snap 520 includes a holding bar 522 and bottom snap 525 includes a retaining wall 527. Sides 530 may also be included on the cover. The sides 530 may be straight members or include holding bars, retaining walls, or other mechanisms to further secure the cover to the mirror. The cover may be colored or incorporate a design to enhance its appearance. If a design is incorporated, it may be a cartoon character to enhance its appeal to children, or, a logo that identifies the tool, a manufacturer, or a dental organization associated with the dental tool. In one embodiment, the design is located on a flat portion 510 of the cover.

FIG. 5B is an illustration of an example embodiment of a cover without sides 530, according to the present invention attached to the mirror. An alternative embodiment consists of a set of colored covers, with or without calibration marks, which overlay the perimeter of the mirror during its intra-oral use, thereby providing a window over most of the mirror surface with the purpose being to enhance the appearance, protect teeth from contact with a non-flexible material and provide a means of mirror identification. The cover may include a small rubber bumper to protect teeth and other objects which the mirror may contact.

Obviously, numerous modifications and variations of the present invention are possible. It is therefore to be understood that within the scope of the appended claims, the invention may be practiced otherwise than as specifically described herein. The mirror of the present invention can eliminate the comparatively inaccurate means of assessing intra-orally the extent of parallelism between non-adjacent teeth, which is commonly performed by carefully moving a small round dental mirror back and forth from one tooth to another while attempting to maintain the mirror in exactly the same plane relative to the eye of the viewer. The size and angulation capability of the present mirror allow it to be placed over the facial, lingual, or occlusal surface of several teeth and view them without intra-oral interferences. The mirror of the present invention, by virtue of its shape and maneuverability also allows unobstructed visualization of occlusal relationships and soft tissue anatomy, not possible with much smaller or much larger mirrors. The plurality of angulations achievable with this mirror allows ease of visualization even with the simultaneous use of a dental drill, cotton rolls, suction apparatus, and other commonly used intra-oral devices. The calibrations placed on or adjacent to the mirrored surface allow greater ease and accuracy in the measurement of lesions and interdental distances than the use of less maneuverable rulers or periodontal probes.

I claim:

1. An improved dental mirror for facilitating accurate visualization and measurement of structures and distances and for facilitating assessment of parallelism between non-adjacent teeth, said dental mirror comprising:

an elongated handle having a longitudinal axis and affixed to one end thereof a mirror frame, said mirror frame supporting a planar mirror of rectangular geometry having a perimeter defined by a pair of major parallel edges and minor parallel edges; and a series of calibrations along said perimeter whereby at least part of one of said edges is calibrated by lines of demarcation;

wherein the mirror, the mirror frame, and elongated handle are appropriately proportioned so as to allow insertion of the mirror into a patient's mouth.

2. The improved dental mirror of claim 1 wherein said lines of demarcation are provided along all edges of the mirror.

3. The improved dental mirror of claim 1 wherein said mirror frame is sized to be larger than said planar mirror creating a border surrounding said perimeter.

4. The improved dental mirror of claim 3 wherein said border is provided with a series of calibrations whereby at least one part of said border is calibrated by lines of demarcation.

5. The improved dental mirror of claim 1 wherein said mirror frame is rigidly affixed to said handle such that said major parallel edges are oriented at one of several predetermined angles with respect to said longitudinal axis.

6. The improved dental mirror of claim 1 wherein said handle is rigidly affixed to said mirror frame supporting said mirror at a first end and rigidly affixed to a second mirror at a second end such that each mirror can be oriented at a different predetermined angle relative to said longitudinal axis.

7. The improved dental mirror of claim 1 wherein said mirror frame is rotatably affixed to the handle such that the orientation between said major parallel edges and said longitudinal axis is adjustable in the plane of the mirror.

8. The improved dental mirror of claim 7 wherein said handle and mirror frame are joined such that said major parallel edges are click set to enable said parallel edges to ratchet in predetermined angle increments with respect to said longitudinal axis.

9. The dental mirror according to claim 1, further comprising a double-ended handle providing a connection point for another type of dental mirror or dental instrument.

10. The dental mirror according to claim 1, wherein said frame has a non-silver colored exterior.

11. The dental mirror according to claim 1 further comprising a cover over at least a portion of the mirror frame.

12. A dental mirror, comprising:
an elongated handle having a longitudinal axis;
a mirror frame affixed to one end of the elongated handle;
a mirror supported by the mirror frame;
a border extending beyond a perimeter of the mirror; and
a series of calibrations along the border;
wherein the mirror, the mirror frame, and the elongated handle are appropriately proportioned so as to allow insertion of the mirror into a patient's mouth.

13. The dental mirror according to claim 12, wherein said series of calibrations comprises a first set of at least 3 parallel lines configured to provide a measurement scale upon which distances between teeth can be measured.

14. A dental mirror, comprising:
a mirror having a reflective surface;
a series of calibrations affixed to at least one edge of the mirror; and
a connection device attached to the mirror;
wherein said connection device comprises a multi-sided object located in a slit of a stem having a threaded part for attaching a handle.

15. The dental mirror according to claim 14, wherein said calibrations comprise etchings on said reflective surface.

16. A dental mirror, comprising:
a mirror having a reflective surface and a back surface;
a frame securing a perimeter of said mirror;
a series of calibrations affixed to at least one edge of said mirror;
a connection device attached to the frame at an off center position adjacent to the back surface;
a handle attached to said connection device;
wherein:
said connection device comprises a multi-sided object, and a bar having a slit separating the bar, said multi-sided object positioned within said slit and held by pressure from opposite sides of said slit;
said multi-sided object comprising a disk having 8 sides;
said calibrations comprising etchings on said reflective surface;
said connection device allowing said mirror to be positioned at different angles relative to an axis of the connection device while staying within a plane of the mirror;
wherein said mirror is rectangular;
said frame has a colored exterior, of shades of red, blue, yellow or green;
said calibrations include a cross hair perpendicular to said calibrations, and said calibrations are etched at least part way across said mirror, and said etchings comprise a line having short and long dashes;
said dental mirror further comprises a cover designed to be placed over at least a portion of said frame and said mirror, said cover having an image of a character and a logo;
said dental mirror has a light coating of a colored substance that does not obscure view of objects in the dental mirror; and
said dental mirror further comprises a circular dental mirror attached at an end of the handle away from the rectangular mirror, said circular dental mirror having a circular frame with calibrations etched on the circular dental mirror and the circular frame, and being adjustable in a plane perpendicular to the circular mirror surface.

17. A dental mirror, comprising:
an elongated handle having a longitudinal axis;
a mirror, having a perimeter, supported by the elongated handle; and
a series of calibrations along the perimeter;
wherein:
said calibrations comprise a first set of at least three parallel lines configured to provide a measurement scale upon which distances between teeth can be measured; and
the mirror and the elongated handle are appropriately proportioned so as to allow insertion of the mirror into a patient's mouth.

18. The dental mirror according to claim 17, wherein said calibrations further comprise a second set of parallel lines perpendicular to the first set.

19. The dental mirror according to claim 17, further comprising:
a mirror frame supporting the mirror;
a border comprising at least a portion of the mirror frame extending beyond the perimeter of the mirror; and
a second series of calibrations on said border.

20. The dental mirror according to claim 19, wherein said mirror frame is rigidly affixed to said handle such that said major parallel edges are oriented at one of several predetermined angles with respect to said longitudinal axis.

21. The dental mirror according to claim 17, wherein said calibrations include at least one line of demarcation.

* * * * *